(12) United States Patent
Bade et al.

(10) Patent No.: US 6,291,698 B1
(45) Date of Patent: Sep. 18, 2001

(54) PROCESS FOR PREPARING VINYL CHLOROSILANES

(75) Inventors: Stefan Bade, Rheinfelden; Bernt Kesper, Wehr; Robert Koell, Rheinfelden; Hartwig Rauleder, Rheinfelden; Uwe Schoen, Rheinfelden, all of (DE)

(73) Assignee: Degussa Huels AG, Frankfurt (DE)

( * ) Notice: Subject to any disclaimer, the term of this patent is extended or adjusted under 35 U.S.C. 154(b) by 0 days.

(21) Appl. No.: 09/556,403

(22) Filed: Apr. 24, 2000

(30) Foreign Application Priority Data

Apr. 22, 1999 (DE) ............................................. 199 18 114

(51) Int. Cl.⁷ ....................................................... C07F 7/08
(52) U.S. Cl. ......................... 556/481; 422/189; 422/190; 422/192; 423/342
(58) Field of Search ........................... 556/481; 623/342; 422/188, 190, 192

(56) References Cited

U.S. PATENT DOCUMENTS

| | | | |
|---|---|---|---|
| 3,666,782 | * | 5/1972 | Mui et al. ............................... 556/481 |
| 5,075,480 | * | 12/1991 | Hange et al. ........................... 556/481 |
| 5,344,950 | * | 9/1994 | Hange et al. ........................... 556/481 |
| 5,808,128 | * | 9/1998 | Fiolitakis ............................... 556/481 |

FOREIGN PATENT DOCUMENTS

| | | |
|---|---|---|
| 936 445 | 12/1955 | (DE) . |
| 20 02 258 | 8/1971 | (DE) . |
| 2 210 189 | 9/1973 | (DE) . |
| 40 01 820 A1 | 7/1991 | (DE) . |
| 40 16 021 A1 | 11/1991 | (DE) . |

* cited by examiner

*Primary Examiner*—Paul F. Shaver
(74) *Attorney, Agent, or Firm*—Oblon, Spivak, McClelland, Maier & Neustadt, P.C.

(57) ABSTRACT

The invention relates to a process for preparing vinyl chlorosilanes, that includes thermally and non-catalytically reacting chlorosilane with vinyl chloride at a temperature of 550 to 700° C. by flowing the chlorosilane and vinyl chloride through a ring-gap space in a ring-gap reactor to produce a reaction gas; the ring-gap space having a cross-sectional area and a volume; and, after the flowing, further reacting, adiabatically, the reaction gas in a second zone to produce a hot reaction gas that contains vinylchlorosilane; wherein the second zone has a cross-sectional area that is greater than the cross-sectional area of the ring-gap space; and wherein the second zone has a volume that is in a ratio to the volume of the ring-gap space of 0.15:1 to 1.5:1. The invention also provides an apparatus for carrying out the above process.

26 Claims, 1 Drawing Sheet

PROCESS FOR PREPARING VINYL CHLOROSILANES

BACKGROUND OF THE INVENTION

1. Field of the Invention

The invention relates to a process for preparing vinyl chlorosilanes by non-catalyzed, thermal reaction of chlorosilanes with vinyl chloride using a reactor combination of a ring-gap reactor equipped with an optionally rotating displacement body and a downstream reactor.

2. Discussion of the Background

Vinyltrichlorosilane is a valuable intermediate which, owing to its four reactive groups, is suitable for many applications. For example, it is used in the sizing of glass fibers and in the manufacture of cable materials.

DE-C 936 445, DE-A 22 10 189 and, in particular, DE-C 20 02 258 disclose that upon passing vinyl chloride/chlorosilane mixtures such as, for example, vinyl chloride/trichlorosilane mixtures, through appropriately-heated, empty ceramic, glass or iron tubes, industrially acceptable yields of vinyl chlorosilanes are achieved. The reaction proceeds purely thermally, i.e., without a catalyst. In the reaction of trichlorosilane with vinyl chloride, the following main reaction proceeds:

Main reaction:

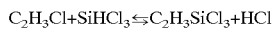

$$C_2H_3Cl + SiHCl_3 \leftrightarrows C_2H_3SiCl_3 + HCl$$

In addition to the main equilibrium reaction, there are the following side reactions and secondary reactions:

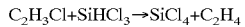
$$C_2H_3Cl + SiHCl_3 \rightarrow SiCl_4 + C_2H_4$$

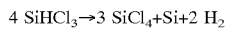
$$4\ SiHCl_3 \rightarrow 3\ SiCl_4 + Si + 2\ H_2$$

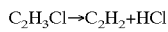
$$C_2H_3Cl \rightarrow C_2H_2 + HCl$$

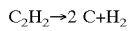
$$C_2H_2 \rightarrow 2\ C + H_2$$

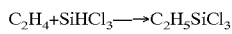
$$C_2H_4 + SiHCl_3 \longrightarrow C_2H_5SiCl_3$$

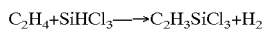
$$C_2H_4 + SiHCl_3 \longrightarrow C_2H_3SiCl_3 + H_2$$

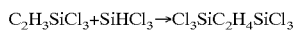
$$C_2H_3SiCl_3 + SiHCl_3 \rightarrow Cl_3SiC_2H_4SiCl_3$$

Despite these side reactions and secondary reactions, according to DE 40 01 820 A1, the selectivity for vinyltrichlorosilane, based on the vinyl chloride used in deficient amounts, depending on the ratio of the starting materials and the degree of conversion, is from 50 to 98% in the case of tubes 122 to 150 cm in length and 25 to 35 mm in diameter, residence times from 0.2 to 20 seconds, reaction temperatures from 400 to 750° C. and pressures from 1 to 3 bar. However, the reactor output (or capacity) of the reactors in this case is only from 0.8 to 3.2 metric tons of vinyltrichlorosilane/month. Selectivity and degree of conversion are inversely proportional to one another; the reactor output passes through a maximum as a function of the degree of conversion. A high selectivity is therefore accompanied with an unsatisfactory and economically unacceptable reactor output at a low degree of conversion. According to DE-A 20 02 258, although increasing the tube diameter up to 50 mm produces an increase in reactor output in proportion to the greater reactor volume, at still greater diameters, the specific reactor output, based on the reactor volume, decreases. It is therefore impossible to increase the space-time yield of vinyltrichlorosilane, or even only maintain it, by increasing the reactor tube diameter to above 50 mm.

An improved process for preparing vinyl chlorosilanes by reacting is chlorosilanes with vinyl chloride is, according to DE 40 01 820 A1, carried out in a ring-gap reactor which has a heatable reaction tube having an internal diameter $d_1$ and in the interior of which is situated a displacement body having an outer diameter $d_2$, and which extends over the entire length of the reaction tube, is axially and symmetrically disposed within the reaction tube and which may optionally rotate. The relationship $d_1 = d_2 + 2a$ applies here, where a is generally at least 1 cm and is always <5 cm. If the displacement body is substantially shorter than the reaction tube, the yield is decreased. This finding corresponds to the teaching of the three abovementioned publications, according to which, in the case of empty tube reactors, the yield falls if the tube diameter exceeds 5 cm. According to DE 40 16 021 A1, the capacity of the reactor and the space-time yield of the process using a ring-gap reactor can be further increased if the reaction components are preheated to 120 to 400° C. prior to entering the reactor. However, even using this measure, much of the reactor volume is still lost in that the reaction components are heated to approximately 550° C., in order that they react adiabatically in the remaining reactor volume.

SUMMARY OF THE INVENTION

One object of the invention is to increase the space-time yield of vinyl chlorosilane.

Another object of the invention is to maintain a high selectivity for the desired vinylchlorosilane at a high degree of conversion.

Another object of the invention is to maintain an economically acceptable high reactor output at a high degree of conversion.

Another object of the invention is to provide a process in which secondary or minor reactions are suppressed.

Another object of the invention is to provide a process in which the deposition of soot and/or elemental silicon is suppressed.

Another object of the invention is to provide a process in which the formation of undesirable high-boilers is suppressed.

These and other objects have been attained by the present invention, the first embodiment of which provides a process for preparing vinyl chlorosilanes, that includes:

thermally and non-catalytically reacting chlorosilane with vinyl chloride at a temperature of 550 to 700° C. by flowing said chlorosilane and vinyl chloride through a ring-gap space in a ring-gap reactor to produce reaction gas; the ring-gap space having a cross-sectional area and a volume; and after the flowing, further reacting, adiabatically, the reaction gas in a second zone;

wherein the second zone has a cross-sectional area that is greater than the cross-sectional area of the ring-gap space; and wherein the second zone has a volume that is in a ratio to the volume of the ring-gap space of 0.15:1 to 1.5:1.

Another embodiment of the invention relates to an apparatus for carrying out the above process, which includes a combination of a ring-gap reactor and a second reactor which is downstream from the ring-gap reactor in a flow direction; wherein the ring-gap reactor includes a ring-gap space having a volume and a cross-sectional area; wherein the second reactor has a cross-sectional area that is greater than the cross-sectional area of the ring-gap space; and wherein the second reactor has a volume that is in a ratio to the volume of the ring-gap space of 0.5:1 to 1.25:1.

BRIEF DESCRIPTION OF THE FIGURES

A more complete appreciation of the invention and many of the attendant advantages thereof will be readily obtained as the same becomes better understood by reference to the following detailed description when considered in connection with the accompanying drawings, wherein.

BRIEF DESCRIPTION OF THE PREFERRED EMBODIMENTS

Figure 1:
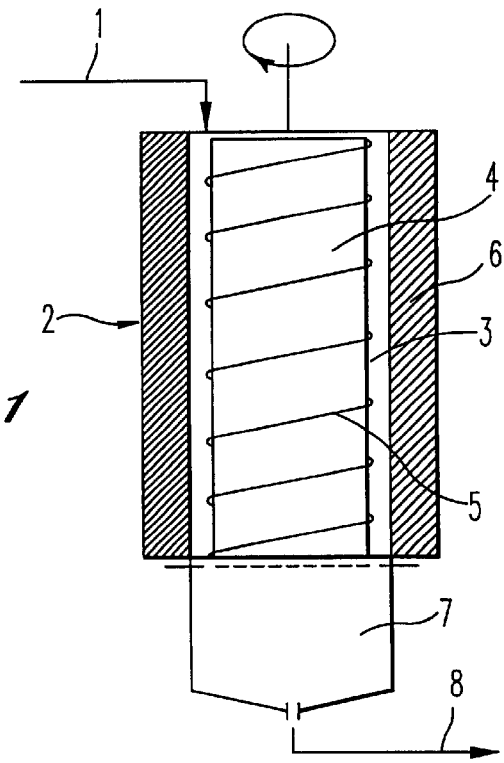
FIG. 1 depicts a preferable apparatus according to the invention which includes a ring-gap reactor and a reactor which follows this and has a greater reactor cross-sectional area. The apparatus according to FIG. 2 additionally has a quenching apparatus.

Various other objects, features and attendant advantages of the present invention will become more appreciated as the same becomes better understood from the following detailed description.

In the novel process, even at high degrees of conversion, a high selectivity for the desired vinyl chlorosilane is combined with an economically acceptable high reactor output. Secondary reactions or side reactions which can lead, inter alia, to the deposition of soot and/or elemental silicon and to the formation of high-boilers, are suppressed. The advantageous action of the division according to the invention of the reaction into two zones or two reactors is surprising, because a substantial part of the reaction takes place in a zone or in a reactor which by far exceeds the critical parameters <50 mm in diameter (in the process according to DE-A 20 02 258) or <50 mm gap width (in the process according to DE 40 01 820 A1). The entire contents of each of the above two references are hereby incorporated by reference.

Preferably, the ring-gap reactor is heatable, and more preferably, the ring-gap reactor is heated.

Preferably, the hot reaction gases are rapidly cooled at the end of the second zone by quenching them with a quenching liquid.

Preferably, the second zone in the process is a second reactor.

Preferably, the second reactor in the apparatus includes an apparatus for quenching the hot reaction gases with a quenching liquid.

Therefore, an apparatus for advantageously carrying out the process most preferably includes a combination of a heatable ring-gap reactor, a second reactor which follows this, in the direction of flow, and has a greater reactor cross-sectional area, the volume of this reactor being in a ratio to the volume of the ring-gap space of from 0.15:1 to 1.5:1, and, if appropriate, an apparatus for quenching with a liquid.

Preferably, vinyltrichlorosilane may be prepared from trichlorosilane and vinyl chloride. Other preferable chlorosilanes having a substitutable hydrogen atom include methylhydrogendichlorosilane and ethylhydrogendichlorosilane.

Preferably, the chlorosilane and vinyl chloride are advantageously used without a diluting liquid or gaseous inert medium and are preferably used in a molar ratio of from 1:1 to 5:1, more preferably from 2:1 to 4:1. Preferably, the reaction components can be introduced into the ring-gap reactor at ambient temperature or, as described in DE 46 16 021 A1, the entire contents of which being hereby incorporated by reference, the reaction components can be introduced into the ring-gap reactor preheated, each alone or in a mixture, to a temperature of 120 to 400° C., more preferably 220 to 400° C., and further heated in the ring-gap reactor. At about 450° C., the exothermic substitution reaction begins which, at about 550° C., achieves a rate such that no further heat supply is necessary; the reaction can therefore proceed essentially adiabatically. Thus, and preferably, the zone of the second reactor (the second zone, as noted above) having the greater cross-sectional area is therefore not heated. As a result of the exothermicity, preferable temperatures of 550 to 700° C., more preferably 550 to 650° C., are established. Each of the above-noted ranges includes all values and subranges therebetween.

The process according to the invention is preferably carried out at pressures of 1.1 to 2.0 bar, more preferably 1.1 to 1.4 bar. The residence times are preferably from 0.2 to 20 seconds, more preferably from 1.0 to 10 seconds. Preferably, they are distributed among the various zones or reactors in relation to their volumes. Each of the above-noted ranges includes all values and subranges therebetween.

As a preferred ring-gap reactor, the reactor described in DE 40 01 820 A1, the entire contents of which being hereby incorporated by reference, can be used. The ring-gap reactor is preferably vertical and preferably has a heatable cylindrical tube having an equally long, axially symmetrically positioned displacement body which can be arranged to be fixed or can rotate about its longitudinal axis, e.g. at from 10 to 100 rpm, more preferably from 20 to 40 rpm. Ring-gap reactors for preparing vinyl chlorosilanes on an industrial scale can preferably be, for example, from 1 to 5 m long, and more preferably from 1.5 to 4.5 m long. The internal diameter of such reactors can preferably be, for example, from 400 to 1200 mm, and more preferably from 500 to 1000 mm. Each of the above-noted ranges includes all values and subranges therebetween.

The inside of the cylindrical tube and the outside of the displacement body form a ring-gap space, in which the starting materials are heated to the starting temperature and the reaction takes place. The displacement body can have a smooth outer wall or can carry on its entire surface, or a part thereof, for example beginning at the entry of the starting material gases, elements which promote the flow rate and/or the vortexing of the reaction gases and thus keep the ring-gap space free from deposits of solid particles.

The elements can be, for example, metal strips which run essentially parallel to the longitudinal axis of the displacement body and have interruptions or are uninterrupted. Alternatively, the continuous or interrupted metal strips can be arranged at an acute angle of from 20 to 50° to the longitudinal axis and then form a guiding spiral. The metal strips can also be mounted as pieces or bumps at regular or irregular intervals on the surface of the displacement body. If a displacement body having a guiding spiral rotates, this expediently takes place in a direction of rotation such that the guiding spiral transports the reaction gases in a direction toward the outlet of the ring-gap reactor. If the metal strips do not form a guiding spiral, but are mounted in such a manner that in no case do they transport the reaction gases, the direction of rotation is irrelevant.

Preferably, the distance between the inner wall of the cylindrical tube and the outer wall of the displacement body is at least 10 mm and at most 50 mm, more preferably at least 15 mm and at most 45 mm. Any elements present which promote the vortexing advantageously project by more than half the gap width into the ring gap. Preferably, the vortex-promoting elements extend over from 60 to 80% of the gap width, more preferably over from 65 to 75% of the gap width. Each of the above-noted ranges includes all values and subranges therebetween.

The cylindrical tube, the displacement body and the elements which promote the vortexing of the reaction gases can be made from most any materials which are stable under the reaction conditions, e.g. of scaling-resistant steels which, in addition to iron, contain as alloy constituents chromium, nickel and titanium and/or molybdenum and/or silicon. Such materials are well-known to one of ordinary skill in the art to which the invention pertains.

The ring-gap reactor is the starting reactor and preferably is provided with a controllable heating apparatus which preferably extends over the entire length of the ring-gap reactor and can preferably be subdivided into a plurality of independently heatable segments. Although it is preferred to heat up the starting material gases (including any of chlorosilane, methylhydrogendichlorosilane, trichlorosilane, and ethylhydrogen-dichlorosilane and vinyl chloride) which enter, optionally and preferably preheated to 120 to 400° C., more preferably to 220 to 400° C. (these ranges including all values and subranges therebetween), the ring-gap reactor, so rapidly that the temperature is about 550° C. and the further reaction proceeds essentially adiabatically without further heat supply, as soon as the reaction gases have passed through from ⅓ to ⅔ of the reactor length, a heating apparatus in the remaining part also ensures the desired flexibility in the event that the starting point of the adiabatic reaction shifts in the direction toward the outlet. The heating is most preferably set in such a manner that the reaction gases enter the second reactor at a temperature of at least 550° C. The reaction gases are most preferably heated indirectly, i.e., by heat transfer through the wall of the cylindrical tube. For example, the cylindrical tube can be provided with an optionally subdivided jacket through which superheated steam or a high-load heat carrier liquid (e.g. a salt melt or liquid metal) can be passed. However, the cylindrical tube is most preferably equipped with an electrical external heater, optionally subdivided into segments.

The ring-gap reactor is followed by a preferably cylindrical second reactor or a second zone which has a greater cross-sectional area than the cross-sectional area of the ring gap in the ring-gap reactor and in which the reaction proceeds adiabatically in the direction toward equilibrium. Most preferably, therefore, this second reactor or this second zone is not heated. Preferably, the cross-sectional area of this second reactor or this second reaction zone is from 5 to 15 times, and more preferably 7.5 to 12.5 times, greater than the ring-gap space in the ring-gap reactor. The second reactor is preferably empty, it contains at least no displacement body and no other moving parts. It is an important feature of the process and reactor of the invention, however, that the volumes of the second reactor or of the second zone are in a ratio to the volume of the ring-gap space of from 0.15:1 to 1.5:1, and preferably from 0.5:1 to 1.25:1. Preferably, the second reactor can be made from the same materials as the ring-gap reactor. Each of the above-noted ranges includes all values and subranges therebetween.

Preferably, the apparatus includes a quenching apparatus in association therewith. If a quenching apparatus is not joined directly to the second reactor, the second reactor preferably has, and preferably on the side opposite to the ring-gap space of the first reactor, a central outlet having a diameter d which is in a ratio of preferably 1:3 to 1:20, more preferably 1:4 to 1:18, to the internal diameter D of the second reactor. These ranges include all values and subranges therebetween. In combination with a guiding spiral on the displacement body, this produces a stable spiral flow which immediately discharges any solid particles from the second reactor.

Preferably, both the reaction gas leaving the first reactor and the hot reaction gas leaving the second reactor or second zone contain vinylchlorosilane. Preferably, the adiabatic reaction begins in the first reactor (ring-gap reactor) and continues in the second reactor or second zone).

The hot reaction gases are preferably quenched with a liquid after they have passed through the second reaction zone. This further improves the reactor output. The quenching apparatus is preferably integrated into the second reactor, but it most preferably is no further than about 1.5 m from the outlet of the second reactor. A conical quenching vessel made of a material stable under the process conditions is most especially preferred, which vessel is joined by its circular orifice directly to the cylindrical second reactor. Preferably, the quenching liquid can be injected into the hot reaction gases in a conical shape in the direction of flow, for example, through a nozzle or plurality of nozzles having a diameter of from 8 to 25 mm, more preferably from 10 to 20 mm. These ranges include all ranges and subranges therebetween.

A preferred quenching liquid is, for example, trichlorosilane or silicon tetrachloride, the desired vinyl chlorosilane, such as vinyltrichlorosilane, for example, or else the crude condensed reaction mixture which generally contains from 25 to 50% by weight of the desired vinyl chlorosilane.

Preferably, the mass flow rate of the quenching liquid is from 2 to 6 times the mass flow rate of the gaseous reaction products (preferably either or both of the reaction gas or the hot reaction gas; most preferably the hot reaction gas), more preferably from 3 to 5 times. These ranges include all values and subranges therebetween. The evaporating quenching liquid cools the reaction gases, whose temperature at the end of the second reaction zone or at the outlet of the second reactor is preferably from 570 to 650° C., rapidly to a temperature of <200° C., more preferably to <175° C., and most preferably <150° C. so that the equilibrium position virtually no longer changes and unwanted secondary reactions virtually no longer take place. Each of the aforementioned ranges includes all values and subranges therebetween. The quenched reaction gases are further cooled and liquefied indirectly. From the liquid phase, the desired vinyl chlorosilane is preferably produced by distillation.

A preferred reactor combination, without a quenching apparatus, for carrying out the process according to the invention is shown in FIG. 1. The mixture of the starting materials 1 is introduced at the top of the vertical ring-gap reactor 2 having the ring gap 3. The reactor has a rotary displacement body 4 on which is mounted a guiding spiral 5. The ring-gap reactor 2 can be heated by the electrical heater 6. The ring-gap reactor 2 is followed by the second reactor 7 which preferably is empty, unheatable and contains no moving parts, at the outlet of which second reactor the reaction mixture 8 is taken off.

Figure 2:
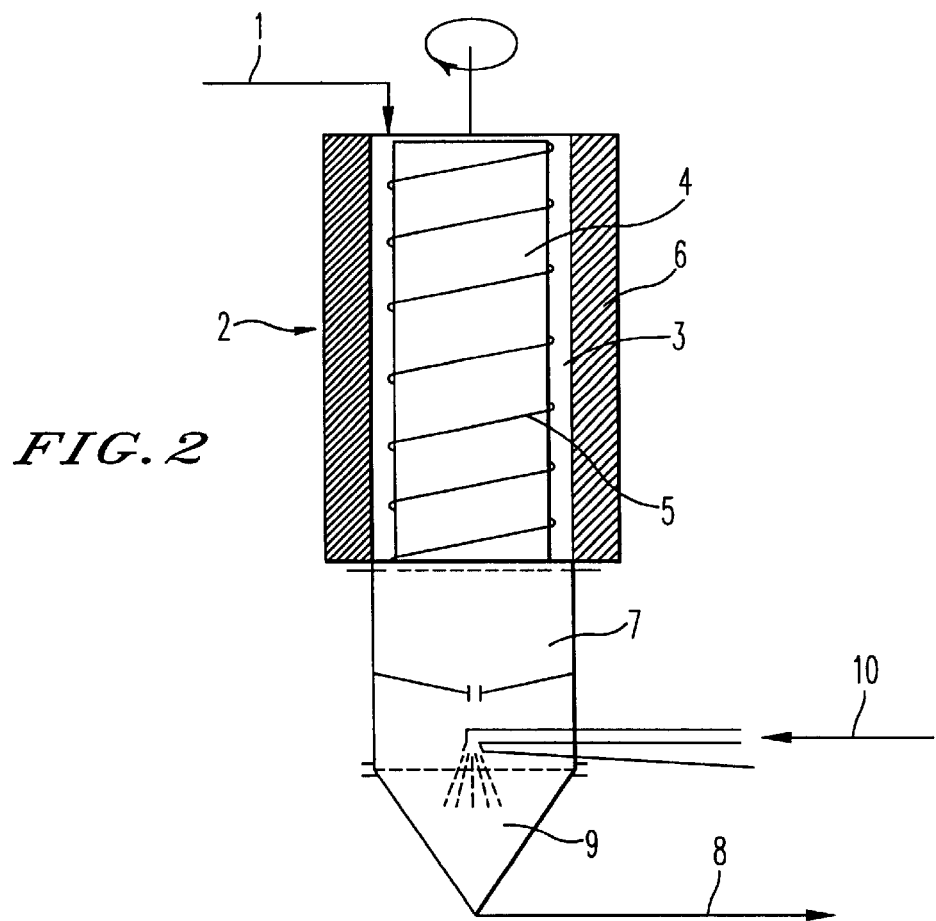

A preferred reactor combination that includes a quenching apparatus is shown in FIG. 2. It differs from the reactor combination of FIG. 1 in that, to the second reactor 7, is joined to a conical quenching vessel 9 which includes a quenching apparatus 10.

EXAMPLES

Having generally described this invention, a further understanding can be obtained by reference to certain specific examples, which are provided herein for purposes of illustration only, and are not intended to be limiting unless otherwise specified.

Example 1

A reactor combination according to FIG. 1 is used. The vertical industrial ring-gap reactor contains an externally electrically heatable cylindrical tube of 2.0 m in length having an internal diameter of 600 mm and a displacement body likewise of 2.0 m in length having an outer diameter of 560 mm. On the displacement body is mounted a guiding spiral having a height of 13 mm which forms an angle of 40° to the longitudinal axis. The ring-gap space is 20 mm wide, the cross-sectional area of the ring-gap space is 3.6 dm$^2$, the ring-gap volume is 72.9 dm$^3$. To the ring-gap reactor is joined a second cylindrical empty reactor of 0.5 m in length having an internal diameter D of likewise 600 mm, whose cross-sectional area is 28.3 dm$^2$ and whose volume is 141.4 dm$^3$. The ratio of the volumes of the ring-gap reactor and the second reactor is 0.52:1; the cross-sectional area of the second reactor is 7.9 times greater than that of the ring-gap space. The second reactor has a circular outlet having an internal diameter d of 100 mm. The ratio D:d is 6:1.

A gaseous mixture, heated to 220° C., of 420 kg/h of trichlorosilane and 70 kg/h of vinyl chloride is fed to the ring-gap reactor at the top; the molar ratio of the starting materials is 2.77. The ring-gap reactor is heated so that a temperature of 580° C. is established in the adiabatic second reactor.

At the outlet of the second reactor, the reaction mixture has the following composition.

| Component | Flow rate (kg/h) |
| --- | --- |
| Vinyl chloride | 9.8 |
| Trichlorosilane | 274.8 |
| Vinyltrichlorosilane | 138.5 |
| Hydrogen chloride | 32.2 |
| Silicon tetrachloride | 20.8 |
| High-boilers and other minor components | 15.5 |

This gives a vinyl chloride conversion rate of 86% and a vinyltrichlorosilane selectivity, based on reacted vinyl chloride, of 89%. The production output of the reactor is 100 metric tons of vinyltrichlorosilane per month. The vinyl chloride conversion rate is approximately equivalent to the theoretically determined equilibrium conversion rate of 87%.

Example 2

The reactor combination described in Example 1 is employed, and a gaseous mixture, heated to 240° C., of 480 kg/h of trichlorosilane and 80 kg/h of vinyl chloride is used; the molar ratio of the starting materials is again 2.77. The ring-gap reactor is heated so that a temperature of 588° C. is established in the adiabatic second reactor.

At the outlet of the second reactor, the reaction mixture has the following composition.

| Component | Flow rate (kg/h) |
| --- | --- |
| Vinyl chloride | 11.8 |
| Trichlorosilane | 311.2 |
| Vinyltrichiorosilane | 154.6 |
| Hydrogen chloride | 34.9 |
| Silicon tetrachloride | 29.2 |
| High-boilers and other minor components | 18.3 |

This gives a vinyl chloride conversion rate of 85% and a vinyltrichlorosilane selectivity, based on reacted vinyl chloride, of 88%. The production output of the reactor is 111 metric tons of vinyltrichlorosilane per month.

Example 3

The reactor combination described in Example 1 is employed, and a gaseous mixture, heated to 260° C., of 540 kg/h of trichlorosilane and 90 kg/h of vinyl chloride is used—the molar ratio of the starting materials is again 2.77. The ring-gap reactor is heated so that a temperature of 601° C. is established in the second adiabatic reactor.

At the outlet of the second reactor, the reaction mixture has the following composition.

| Component | Flow rate (kg/h) |
| --- | --- |
| Vinyl chloride | 13.6 |
| Trichlorosilane | 343.8 |
| Vinyltrichlorosilane | 172.1 |
| Hydrogen chloride | 38.8 |
| Silicon tetrachloride | 37.9 |
| High-boilers and other minor components | 23.8 |

This gives a vinyl chloride conversion rate of 85% and a vinyltrichlorosilane selectivity, based on reacted vinyl chloride, of 87%. The production output of the reactor is 124 metric tons of vinyltrichlorosilane per month.

Example 4

The reactor combination described in Example 1 is employed, and a gaseous mixture, heated to 260° C., of 600 kg/h of trichlorosilane and 100 kg/h of vinyl chloride is used; the molar ratio of the starting materials is again 2.77. The ring-gap reactor is heated so that a temperature of 642° C. is established in the second adiabatic reactor.

At the outlet of the second reactor, the reaction mixture has the following composition.

| Component | Flow rate (kg/h) |
| --- | --- |
| Vinyl chloride | 14.8 |
| Trichlorosilane | 440.4 |
| Vinyltrichlorosilane | 142.7 |
| Hydrogen chloride | 32.2 |
| Silicon tetrachloride | 47.8 |
| High-boilers and other minor components | 22.1 |

This gives a vinyl chloride conversion rate of 85% and a vinyltrichlorosilane selectivity, based on reacted vinyl chloride, of 65%. The production output of the reactor is 103 metric tons of vinyltrichlorosilane per month.

This example shows, in comparison with the preceding examples, that the production output of the reactor combination and the vinyltrichlorosilane selectivity are decreased as a result of the higher throughput and the higher temperature in the adiabatic second reactor.

Example 5

The reactor combination described in Example 1 is employed, but, instead of the guiding spiral, 13 mm high bumps having a 50 mm diameter are disposed on the displacement body at irregular intervals of from 10 to 30 cm. A gaseous mixture, heated to 220° C., of 420 kg/h of trichlorosilane and 70 kg/h of vinyl chloride is used; the molar ratio of the starting materials is again 2.77. With the same heating as in Example 2, a temperature of 571° C. is established in the second adiabatic reactor.

At the outlet of the second reactor, the reaction mixture has the following composition.

| Component | Flow rate (kg/h) |
| --- | --- |
| Vinyl chloride | 16.1 |
| Trichlorosilane | 239.5 |
| Vinyltrichlorosilane | 123.9 |
| Hydrogen chloride | 28.1 |
| Silicon tetrachloride | 18.5 |
| High-boilers and other minor components | 13.9 |

This gives a vinyl chloride conversion rate of 77% and a vinyltrichlorosilane selectivity, based on reacted vinyl chloride, of 89%. The production output of the reactor is 89 metric tons of vinyltrichlorosilane per month.

This example shows, in comparison with Example 1, that the bumps instead of the guiding spiral lead to a lower adiabatic temperature and to a lower vinyl chloride conversion rate, while the vinyltrichlorosilane selectivity remains unchanged.

Example 6 (Comparative Example)

A vertical industrial ring-gap reactor is employed without a second adiabatic reactor. The reactor includes an externally electrically heatable cylindrical tube of 2.5 m in length having an internal diameter of 600 mm and a displacement body of likewise 2.5 m in length and a diameter of 560 mm. Bumps are mounted on the displacement body, as described in Example 5. The ring gap is 20 mm wide.

A gaseous mixture, heated to 220° C., of 420 kg/h of trichlorosilane and 70 kg/h of vinyl chloride is used; the molar ratio of the starting materials is again 2.77. The ring-gap reactor is heated so that a temperature of 578° C. is established 10 cm above the exit.

At the outlet of the second reactor, the reaction mixture has the following composition.

| Component | Flow rate (kg/h) |
| --- | --- |
| Vinyl chloride | 25.9 |
| Trichlorosilane | 311.1 |
| Vinyltrichlorosilane | 102.6 |
| Hydrogen chloride | 23.1 |
| Silicon tetrachloride | 13.9 |
| High-boilers and other minor components | 13.4 |

This gives a vinyl chloride conversion rate of 63% and a vinyltrichlorosilane selectivity, based on reacted vinyl chloride, of 90%. The production output of the reactor is 74 metric tons of vinyltrichlorosilane per month. Although the vinyltrichlorosilane selectivity is high, the vinyl chloride conversion rate and the reactor output are unsatisfactory.

Example 7

A reactor combination according to FIG. 2 is used. The ring-gap reactor includes a cylindrical tube having an internal diameter of 600 mm and a displacement body having an outer diameter of 560 mm, each of which are 2.0 m in length. On the displacement body is mounted a guiding spiral having a diameter of 13 mm, which forms an angle of 400 to the longitudinal axis. The ring gap is 20 mm wide. The ring-gap cross-sectional area is 3.6 dm$^2$, the ring-gap volume is 72.9 dm$^3$. To the ring-gap reactor is joined a second downwardly conically ending reactor of 0.5 m in length likewise having an internal diameter of 600 mm. The cross-sectional area of this reactor is, at the transition from the ring-gap reactor to the second reactor, 28.3 dm$^2$, and the volume is 142.4 dm$^3$. The ratio of the volumes of the ring-gap reactor and the second reactor is 0.52:1, and the cross-sectional area of the second reactor is 7.9 times greater than that of the ring gap. The second reactor is followed by the conical quenching vessel having a quenching nozzle.

A gaseous mixture, heated to 350° C., of 600 kg/h of trichlorosilane and 100 kg/h of vinyl chloride is used; the molar ratio of the starting materials is again 2.77. The ring-gap reactor is heated so that a temperature of 635° C. is established in the second adiabatic reactor. 2000 kg/h of condensed liquid reaction mixture are introduced through the quenching nozzle, as a result of which the temperature of the reaction mixture is decreased to 82° C.

The reaction mixture, minus the quenching stream, has the following composition.

| Component | Flow rate (kg/h) |
| --- | --- |
| Vinyl chloride | 14.9 |
| Trichlorosilane | 380.2 |
| Vinyltrichlorosilane | 193.3 |
| Hydrogen chloride | 43.6 |
| Silicon tetrachloride | 51.8 |
| High-boilers and other minor components | 16.2 |

This gives a vinyl chloride conversion rate of 85% and a vinyltrichlorosilane selectivity, based on reacted vinyl chloride, of 88%. The production output of the reactor is 139 metric tons of vinyltrichlorosilane per month. Comparison with Example 4 shows that the quench brings about a markedly higher vinyltrichlorosilane selectivity and thus a markedly higher reactor output for the same vinyl chloride conversion rate.

This application is based on German application DE 199 18 114.4, filed Apr. 22, 1999, the entire contents of which are hereby incorporated by reference.

Having now fully described this invention, it will be apparent to one of ordinary skill in the art that many changes and modifications can be made thereto without departing from the spirit or scope of the invention as set forth herein.

What is claimed is:

1. A process for preparing vinyl chlorosilanes, comprising:

thermally and non-catalytically reacting chlorosilane with vinyl chloride at a temperature of 550 to 700° C. by flowing said chlorosilane and vinyl chloride through a ring-gap space in a ring-gap reactor to produce a reaction gas; the ring-gap space comprising a cross-sectional area and a volume; and after the flowing, further reacting, adiabatically, the reaction gas in a second zone to produce a hot reaction gas comprising vinylchlorosilane;

wherein the second zone comprises a cross-sectional area that is greater than the cross-sectional area of the ring-gap space; and wherein the second zone comprises a volume that is in a ratio to the volume of the ring-gap space of 0.15:1 to 1.5:1.

2. The process as claimed in claim 1, wherein the ring-gap reactor comprises an optionally rotatable displacement body which is arranged axially symmetrical in a cylindrical tube.

3. The process as claimed in claim 2, wherein the ring-gap space is formed between the displacement body and the ring-gap reactor.

4. The process as claimed in claim 2, wherein the displacement body comprises over its entire length or a part thereof elements which promote the vortexing of the reaction gas, the flow rate of the reaction gas, or both.

5. The process as claimed in claim 4, wherein the elements comprise the form of a spiral or bumps.

6. The process as claimed in claim 4, wherein the elements have a height of 60 to 80% of the width of the ring-gap space.

7. The process as claimed in claim 1, wherein the ring-gap space is 10 to 50 mm wide.

8. The process as claimed in claim 1, wherein the ring-gap space is 20 to 50 mm wide.

9. The process as claimed in claim 1, wherein the second zone comprises, at a side thereof opposite to the ring-gap space of the ring-gap reactor, a central outlet comprising a diameter d; wherein second zone further comprises an internal diameter D; and wherein said diameter d is in a ratio to said internal diameter D ranges from 1:3 to 1:20.

10. The process as claimed in claim 1, wherein the temperature of the adiabatic reaction ranges from 550 to 650° C.

11. The process as claimed in claim 1, wherein the pressure ranges from 1.1 bar to 2.0 bar.

12. The process as claimed in claim 1, wherein the pressure ranges from 1.1 bar to 1.4 bar.

13. The process as claimed in claim 1, further comprising a residence time of 0.2 to 20 seconds.

14. The process as claimed in claim 1, further comprising a residence time of 1.0 to 10 seconds.

15. The process as claimed in claim 1, wherein a molar ratio of chlorosilane to vinyl chloride ranges from 1:1 to 5:1.

16. The process as claimed in claim 1, wherein the chlorosilane is trichlorosilane.

17. The process as claimed in claim 1, further comprising preheating the chlorosilane and vinyl chloride either separately or in admixture to a temperature of 120 to 400° C.

18. The process as claimed in claim 1, further comprising preheating the chlorosilane and vinyl chloride either separately or in admixture to a temperature of from 220 to 400° C.

19. The process as claimed in claim 1, further comprising rapidly cooling the hot reaction gas by quenching the hot reaction gas with a quenching liquid.

20. The process as claimed in claim 19, wherein the quenching liquid comprises as least one selected from the group consisting of trichlorosilane, silicon tetrachloride, vinyl chlorosilane, a liquid reaction mixture, and mixtures thereof.

21. The process as claimed in claim 19, wherein the mass flow rate of the quenching liquid is from two to six times the mass flow rate of the reaction gas.

22. The process as claimed in claim 19, wherein said quenching is carried out in a quenching zone that is either directly connected to the second zone or is located not greater than about 1.5 m from an outlet of the second zone.

23. The process as claimed in claim 19, wherein said quenching liquid is injected into the hot reaction gas in a conical shape in the direction of flow by a nozzle or plurality of nozzles having a diameter of 8 to 25 mm.

24. An apparatus for carrying out the process according to claim 1, comprising:
a combination of a ring-gap reactor and a second reactor which is downstream from the ring-gap reactor in a flow direction; wherein the ring-gap reactor comprises a ring-gap space having a volume and a cross-sectional area; wherein the second reactor comprises a cross-sectional area that is greater than the cross-sectional area of the ring-gap space; and wherein the second reactor comprises a volume that is in a ratio to the volume of the ring-gap space of 0.5:1 to 1.25:1.

25. The apparatus as claimed in claim 24, wherein said second reactor further comprises a quenching apparatus.

26. An apparatus for preparing vinylchlorosilanes, comprising:
a combination of a ring-gap reactor in which vinyl chloride and a chlorosilane are thermally and non-catalytically reacted at a temperature of 550 to 700° C. in the ring gap space of the reactor having a volume and a cross-sectional area; and a second reactor having a cross-sectional area that is greater than the cross-sectional area of the ring-gap space and which has a volume in a ratio relationship to the volume of the ring-gap space of 0.5:1 to 1.25:1 in which the material discharged from the ring-gap reactor is further reacted adiabatically, said second reactor being downstream from the ring-gap reactor in a flow direction.

* * * * *